United States Patent [19]
Yamamoto et al.

[11] Patent Number: 5,676,847
[45] Date of Patent: Oct. 14, 1997

[54] METHOD FOR RECOVERING CRYSTALS FROM SLURRY WITH WASH WATER RECYCLE MEANS

[75] Inventors: Ryoichi Yamamoto; Toshiyuki Sakata; Hiroshi Suzuki; Etsuro Okamoto, all of Kuga-Gun, Japan

[73] Assignee: Mitsui Petrochemical Industries, Ltd., Tokyo, Japan

[21] Appl. No.: 246,714

[22] Filed: May 20, 1994

[30] Foreign Application Priority Data

May 24, 1993 [JP] Japan .................. 5-120301

[51] Int. Cl.$^6$ .................................................. B01D 33/06
[52] U.S. Cl. .................. 210/784; 210/805; 210/194; 210/217; 210/403; 210/404; 210/398
[58] Field of Search .................. 210/784, 805, 210/194, 217, 402, 403, 404, 398

[56] References Cited

U.S. PATENT DOCUMENTS

| | | | |
|---|---|---|---|
| 3,409,139 | 11/1968 | Jackson et al. | 210/414 |
| 4,255,264 | 3/1981 | Madsen | 210/404 |
| 5,093,001 | 3/1992 | Ueda | 210/403 |
| 5,175,355 | 12/1992 | Streich et al. | |

FOREIGN PATENT DOCUMENTS

| | | |
|---|---|---|
| 0406424 | 1/1991 | European Pat. Off. |
| 1482148 | 4/1966 | France |
| 1278402 | 9/1968 | Germany |
| 1025371 | 4/1966 | United Kingdom |

OTHER PUBLICATIONS

BHS–Fest Druck–Vakuum Filter, *Huttenwerk Sonthofen*, 1961, Complete Document in German (and English Translation).

*Primary Examiner*—Robert A. Dawson
*Assistant Examiner*—Robert James Popovics
*Attorney, Agent, or Firm*—Birch, Stewart, Kolasch & Birch, LLP

[57] ABSTRACT

A method for recovering crystals from a crystal-containing slurry, which comprises supplying the slurry to a rotary filter having a rotating cylindrical filter medium, filtering the supplied slurry in a filtering region to retain the crystals on the filter medium and washing the filter cake formed on the rotating filter medium repeatedly in a plurality of washing regions by spraying a washing liquid onto the cake in each region by supplying any one of washing regions on the aft side in the rotating direction of the filter medium with the spent washing liquid of the washing region adjacent to said one washing region on the fore side in the rotating direction.

3 Claims, 3 Drawing Sheets

METHOD FOR RECOVERING CRYSTALS FROM SLURRY WITH WASH WATER RECYCLE MEANS

FIELD OF THE INVENTION

The present invention relates to a method and an apparatus for recovering crystals from a slurry containing crystals of, for example, terephthalic acid.

BACKGROUND OF THE INVENTION

Terephthalic acid used as a starting material of polyethylene terephthalate and the like is produced by oxidizing paraxylene with a molecular oxygen-containing gas in a reaction medium based on acetic acid, wherein the resulting terephthalic acid will deposit in the reaction liquor in a crystalline form. Since the so-formed slurry of the crystalline terephthalic acid contains also the acetic acid solvent, the unreacted paraxylene, by-products and the catalyst components, it is necessary to separate only the terephthalic acid crystals from the slurry in order then to recover the terephthalic acid.

FIG. 3 shows a schematic sequence diagram for a conventional method for recovering terephthalic acid crystals from such a slurry. In FIG. 3, the numeral 101 denotes an oxidizing reactor, to which a raw material mixture 102 composed of paraxylene as the starting material, acetic acid as the reaction medium and the catalyst is supplied, while supplying thereto at the same time a molecular oxygen-containing gas 103 to cause oxidation of the paraxylene into terephthalic acid.

In this conventional technique for recovering terephthalic acid crystals, the crystal-containing slurry 104 formed in the oxidizing reactor 101 is transferred to a first stage solid/liquid separator 105 to effect a primary solid/liquid separation to separate the crystals from the liquid phase. The liquid phase 106 composed mainly of acetic acid separated here is returned to the oxidizing reactor 101, while the crude crystals 107 are forwarded to a re-disperser 108, where the crystals are suspended again in a medium of acetic acid 109 fed thereto in order to dissolve out the contaminants included in the crude crystal mass. The resulting reformed slurry 110 is then subjected to a secondary liquid/solid separation to separate the crystals from the liquid phase in a second stage solid/liquid separator 111. The separated liquid phase 112 composed mainly of acetic acid is transferred to the oxidizing reactor 101, while the purified crystals 113 are forwarded to a drier 114. The dried crystals 115 are stored in a silo 116. The recovered crystals 117 are then conveyed to a disperser 118, whereto water 119 is also supplied and is mixed with the crystals 117 to form an aqueous slurry 120 which is guided then to a refinery system to refine the crystals.

The conventional technique for recovering crystals from a slurry requires thus a large number of process steps with a correspondingly large number of devices and instruments, resulting in higher production costs for the final product.

On the other hand, a proposal is disclosed in Japanese Patent Application Kokai No. 299618/1989 (corresponding to U.S. Pat. No. 5,093,001 and to EPC 04,064,424 A1) for a method of recovering crystals from a crystal-containing slurry using a rotary sucking filter, in which the slurry is supplied to the rotary sucking filter and is subjected to a sucking filtration on a rotating filter medium, while pressurizing the slurry side thereof, with subsequent water washing of the resulting filtered cake on the filter medium.

This proposed method exhibits disadvantages, for example, occurrence of a large amount of waste wash water containing considerable amount of acetic acid in a low concentration, which adds problems to the waste water treatment.

SUMMARY OF THE INVENTION

An object of the present invention is to provide a novel method for recovering crystals from a crystal-containing slurry on a simple process mechanism using a simplified apparatus with less amount of wash water, in order to solve the problems of the technique explained above, which method permits an effective reclamation of the contaminant components included in the separated crude crystals.

Another object of the present invention is to provide a novel apparutus for realizing the above method, which apparatus has a simple construction and enables the separation and recovery of crystals in an efficient manner from a crystal-containing slurry by a simple operation.

Thus, in the present invention, crystals are recovered from a crystal-containing slurry using a rotary filter having a rotating cylindrical filter medium, by supplying the crystal-containing slurry to the rotary filter, filtering the supplied slurry in a filtering region of the rotating filter medium so as to separate the crystals as a filter cake on the filter medium, washing the filter cake on the rotating filter medium in a plurality of washing regions by supplying a washing liquid to, and separating the spent washing liquid from, each of the washing regions in such a manner, that a fresh washing liquid is supplied to the washing region of the forefront in the moving direction of the rotating filter medium, while supplying any one of the washing regions on the aft side of said forefront, seen in the moving direction of the rotating filter medium, with the spent washing liquid separated in the washing region adjacent to said one washing region on the fore side, seen in the moving direction of the filter medium, and collecting the washed filter cake from the filter medium.

The apparatus for recovering crystals according to the present invention comprises a rotary filter having a casing for receiving the slurry supplied, a cylindrical filter medium rotating within the casing so that its cylindrical surface passes through, in order, a filtering region for separating the crystals from the slurry as a filter cake, a plurality of washing regions for washing the filter cake, and a filter cake removing region for discharging out the washed filter cake, a plurality of spraying units for spraying washing liquids onto the filter cake on the filter medium, each of said spraying units being disposed outside the cylindrical filter medium in each of the washing regions, a spent washing liquid receiver provided for each spraying unit except that of the washing region rearmost in the moving direction of the filter medium, said receiver being disposed inside the cylindrical filter medium in the corresponding washing region and means for collecting the washed filter cake from the filter medium in the filter cake removing region; and means for supplying a fresh washing liquid to the spraying unit of the washing region of forefront in the moving direction of the rotating filter medium and supplying any one of the spraying units of the washing regions on the aft side of said forefront, seen in the moving direction of the rotating filter medium, with the spent washing liquid from the spent washing liquid receiver of the washing region neighboring the washing region of said one spraying unit on the fore side, seen in the moving direction of the filter medium.

DETAILED DESCRIPTION OF THE INVENTION

Figure 1:
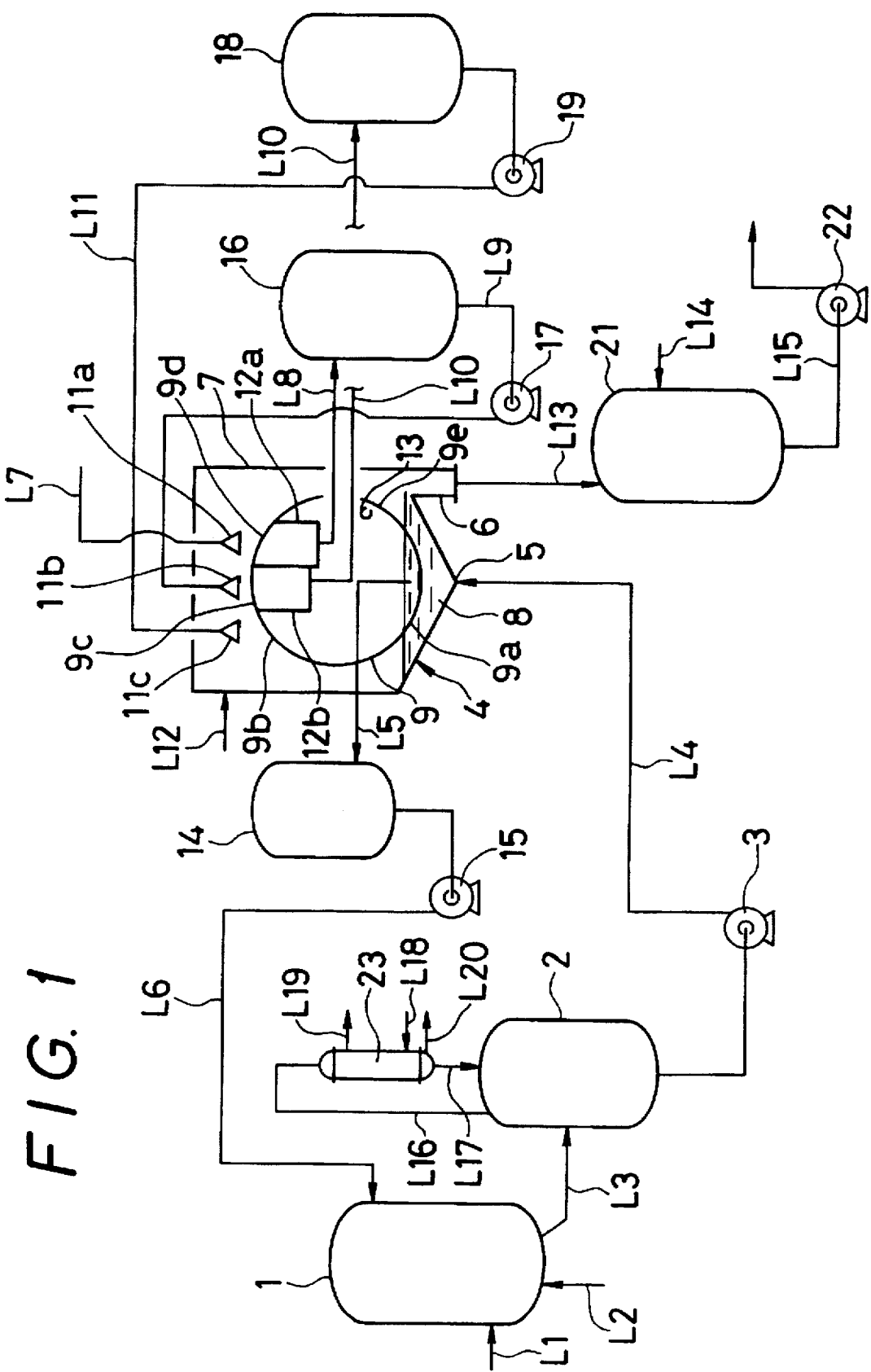
FIG. 1 is a schematic flow diagram for a preferred embodiment of the apparatus for recovering crystals from a slurry according the present invention.

The method as well as the apparatus for use therefor according to the present invention are adapted especially for recovering terephthalic acid crystals, although they can be applied to recovering crystalline products, such as hydroquinone, resorcin etc., from slurries containing them.

For the rotary filter to be employed according to the present invention, a conventional rotary vacuum filter containing a rotating cylindrical filter medium operated by maintaining a reduced pressure inside the filter medium for establishing the filtering pressure drop across the filter medium may be used, though it is rather preferred to use a rotary pressure filter operated by pressurizing the outside of its rotating filter medium for establishing the filtering pressure drop. A rotary pressure/sucking filter may also be used. In a rotary vacuum filter operated by maintaining a reduced pressure inside the rotating filter medium, a part of the solvent of the slurry becomes vaporized due to the lowering of the pressure, whereby the slurry temperature is lowered by being deprived of the latent heat of vaporization, so that the solubility of the solutes existing at their saturation points in the solvent of the slurry is decreased to force deposition thereof in the form of fine particles which fill up the liquid flow paths between the solid particles in the filter cake and cause stuffing of the filter medium. In contrast thereto, a rotary pressure filter and a rotary pressure/sucking filter exhibit less tendency to stuffing of the filter medium than does a rotary vaccum filter, since occurrence of slurry temperature lowering due to the solvent vaporization is avoided in the rotary pressure/sucking filter.

According to the present invention, the filter cake formed on the filter medium is washed in a series of steps on the rotating filter medium in a plurality of washing regions subsequent to the filtering region of the rotary filter to a considerable degree, so that the number of solid/liquid separators and their accessories required for recovering the crystals are reduced as compared with those of the conventional techniques. By way of example, in the case of recovering terephthalic acid crystals by the method according to the present invention, the primary slurry containing the crude terephthalic acid crystals from an oxidizing reactor is filtered by a rotary filter on a rotating filter medium and the resulting filter cake is washed several times on the rotating filter medium with a washing liquid, whereupon the washed filter cake is re-suspended to form a secondary slurry which is sent directly to a disperser for forming the starting slurry to be supplied to the crystal refinery system. In this manner, a series of a primary solid/liquid separator, a re-disperser, a drier and a silo with their accessories in the first process step of the conventional technique are dispensed with.

The contaminant components included in the filter cake can be recovered and reclaimed effectively by washing the filter cake on the rotating filter medium in a plurality of washing regions, by supplying a washing liquid to, and separating the spent washing liquid from, each of the washing regions in such a manner that fresh washing liquid is supplied to the washing region of the forefront in the moving direction of the rotating filter medium, while supplying any one of the washing regions on the aft side of said forefront, seen in the moving direction of the rotating filter medium, with the spent washing liquid separated in the washing region adjacent to said one washing region on the fore side, seen in the moving direction of the filter medium, and recycling the spent washing liquid from the washing region rearmost in the moving direction of the filter medium to the slurry preparation step together with the filtrate of the filtering region. In recovering terephthalic acid crystals by the method according to the present invention, the spent washing liquid from the final washing region, namely, the washing region rearmost in the rotating direction of the filter medium, has a considerably higher acetic acid concentration due to the incremental accumulation thereof by the repeated use of the spent washing liquid from the preceding regions as the washing liquid successively. This spent washing liquid from the washing region rearmost in the rotating direction of the filter medium can be recycled to the oxidizing reactor to reuse it as the reaction medium for the oxidation of paraxylene.

In this manner, by the method and apparatus for recovering crystals from a slurry according to the present invention, the procedures of repeated washing of the filter cake and solid/liquid separation of the slurry are realized in one and the same rotary filter, so that the number of solid/liquid separators to be incorporated and the accessories for them can be reduced, whereby the construction of the entire recovery system can be simplified and an economization of energy and an improvement of the operation of the system are attainable.

PREFERRED EMBODIMENT OF THE INVENTION

FIG. 1 shows a schematic flow diagram of an apparatus for recovering crystals from a crystal-containing slurry accoding to a preferred embodiment of the present invention. In FIG. 1, the numeral 1 denotes an oxidizing reactor which is constructed so as to realize an oxidizing reaction of the raw material by supplying thereto the starting raw material mixture via a supply line L1, and a molecular oxygen-containing gas via a gas supply line L2. An exhaust line L3 for discharging out the resulting slurry of the oxidizing reaction communicates from the bottom of the oxidizing reactor 1 to a flash drum 2. A slurry supply line L4 including a slurry pump 3 communicates from the bottom of the flash drum 2 to a rotary pressure filter 4 at a slurry inlet 5.

The rotary pressure filter 4 having the slurry inlet 5 at its bottom has a casing 7 provided with a filter cake discharge gate 6 arranged downwards. A horizontal cylindrical filter medium 9 is disposed within the casing 7 of the rotary pressure filter 4 with its lower portion being immersed in a sump 8 of the slurry supplied thereto so as to constitute a filtering region 9a and is rotatingly driven clockwise in FIG. 1 at a constant speed by a not-shown motor under intermediation by a reduction gear. A plurality of spray nozzles 11a, 11b, 11c constituting a spraying unit for spraying a washing liquid onto the filter cake on the filter medium are disposed outside the rotating filter medium 9 each correspondingly, but in the reverse sense, in each of a plurality of washing regions 9b, 9c, 9d provided subsequently to the filtering region 9a above the slurry sump 8 and allotted successively in a row in the rotating direction of the filter medium. As a spent washing liquid receiving means for receiving the spent washing liquid sprayed onto the filter cake outside the filter medium and passed therethrough to the inside thereof, spent washing liquid receivers 12a, 12b are disposed inside the cylindrical filter medium in a paired relation with the spray nozzles 11a, 11b except the spray nozzle 11c of the washing region rearmost in the rotating direction. A gas blow nozzle 13 is located inside the filter medium 9 in a filter cake removal region 9e at a portion adjacent the cake discharge gate 6 and serves for blowing $N_2$ gas from inside to the filter cake layer to remove it off the filter medium 9.

An exhaust line L5 for exhausting the spent washing liquid for the rearmost spray nozzle in the rotating direction together with the filtrate collected in the bottom portion of the rotating filter medium communicates therefrom to a filtrate reservoir 14 which is connected with the oxidizing reactor 1 by a line L6 having a pump 15. A line L7 is connected with the nozzle 11a in order to supply pure water as the fresh washing liquid. The receiver 12a is connected with a first spent washing liquid storage tank 16 via a line L8 and the bottom of the storage tank 16 is connected with the spray nozzle 11b via a line L9 having a pump 17. The receiver 12b is connected with a second spent washing liquid storage tank 18 via a line L10 and the bottom of the storage tank 18 is connected with the spray nozzle 11c via a line L11 having a pump 19. The casing 7 is connected at its upper portion with a line L12 for pressurizing the outside of the rotating filter medium and its cake discharge gate 6 is connected with a disperser 21 via a line L13. The disperser 21 is connected with a line L14 for supplying pure water thereto and at its bottom with a line L15 having an interposed pump 22 and communicating to a refinery system.

The flash drum 2 is connected with a condenser 23 by lines L16 and L17 for cooling the vapor from the flash drum 2 to condense it and to return the condensate thereto. The condenser 23 is connected with lines L18, L19 and L20 for supplying the cooling water thereto, for discharging the spent cooling water therefrom and for exhausting the trapped non-condensing gas out of it, respectively.

The recovery of the crystals from the slurry using the apparatus explained above is carried out as follows:

The oxidizing reactor 1 is supplied with a raw material mixture composed of paraxylene as the starting material, acetic acid as the solvent and a catalyst via the line L1 and also with a molecular oxygen-containing gas, such as the air, via the line 2 and in which paraxylene is oxidized by the molecular oxygen into terephthalic acid.

The resulting reaction product mixture in the form of a slurry is sent from the oxidizing reactor 1 via the line L3 to the flash drum 2, where it is exposed to a reduced pressure and is flashed to cause a temperature decrease. The vapor phase is cooled by the condenser 23 to condense the condensible components into a condensate which is returned to the flash drum 2 via the line L17 and the non-condensible gas is exhausted out via the line L20. The slurry left in the flash drum 2 is guided via the line L4 to the slurry inlet 5 of the rotary pressure filter 4 by the pump 3.

By rotating the horizontal cylindrical filter medium 9 clockwise (seen in FIG. 1) within the casing 7 of the rotary pressure filter 4 while pressurizing the outside of the cylindrical filter medium 4 by pressing an inert gas, such as $N_2$, into the casing 7, the slurry contacting with the cylindrical rotating filter medium 9 in its bottom portion constituting the filtering region 9a immersed in the slurry is subjected to filtration by the pressure gradient across the filter medium to retain the crystals on the filter medium 9 as the filter cake while successively moving upwards in accordance with the rotation of the filter medium 9. The filter cake on the filter medium 9 passes then through the washing regions 9b, 9c and 9d in which it is washed with a washing liquid to remove off the contaminant components included therein. Here, pure water is supplied as the washing liquid via the line L7 to the spray nozzle 11a in the washing region 9d of the forefront in the rotating direction of the filter medium 9 and is sprayed to wash the filter cake. The spent washing water passed through the filter cake and the filter medium and collected in the receiver 12a is guided through the line L8 to the first spent washing liquid storage tank 16, from which it is supplied to the spray nozzle 11b of the washing region 9c adjacent to the above-mentioned forefront washing region 9d in the aft side in the rotating direction of the filter medium by the pump 17 and is sprayed to wash the filter cake in the washing region 9c. The spent washing water collected in the receiver 12b of the washing region 9c is guided through the line L10 to the second spent washing liquid storage tank 18, from which it is supplied to the spray nozzle 11c of the washing region 9b rearmost in the rotating direction of the filter medium by the pump 19 and is sprayed to wash the filter cake.

By supplying, in this manner, any one of the washing regions on the aft side of the washing region of the forefront, seen in the moving direction of the rotating filter medium with the spent washing water separated in the washing region adjacent to the said one washing region on the fore side, seen in the moving direction of the filter medium, the concentration of the contaminant components, such as acetic acid and unreacted starting material, in the spent washing water becomes increased successively in the washing regions towards aft the rotating direction of the filter medium. The spent washing water of the washing region 9b rearmost in the rotating direction, which has the highest concentration of such contaminant components, is gathered with the filtrate from the filtering region 9a in the bottom portion of the horizontal cylindrical filter medium, from which it is recycled, namely, together with the filtrate, to the oxidizing reactor 1 via the line L6 by the pump 15 for reuse in the oxidation reaction.

In this manner, the filter cake of crystals retained on the rotating filter medium in a layer is cleaned to a considerable degree by a repeated washing (three times in this embodiment) in the washing regions 9b–9d under separation of each portion of spent washing water from the crystals with final washing by pure water, so that the contaminant components, such as acetic acid etc., occluded in between the crystals can efficiently be removed. The washed filter cake left on the rotating filter medium in a layer is blown off from the filter medium 9 in the filter cake removing region 9e by blowing an inert gas, such as $N_2$, gas, from inside onto the filter cake layer using a gas blowing nozzle 13 and the so-removed filter cake is discharged from the cake discharge gate 6 into the disperser 21, where the filter cake is re-suspended in pure water supplied thereto via the line L14 to form a secondary slurry which is supplied to the refinery system via the line L15 by the slurry pump 22.

Figure 2:
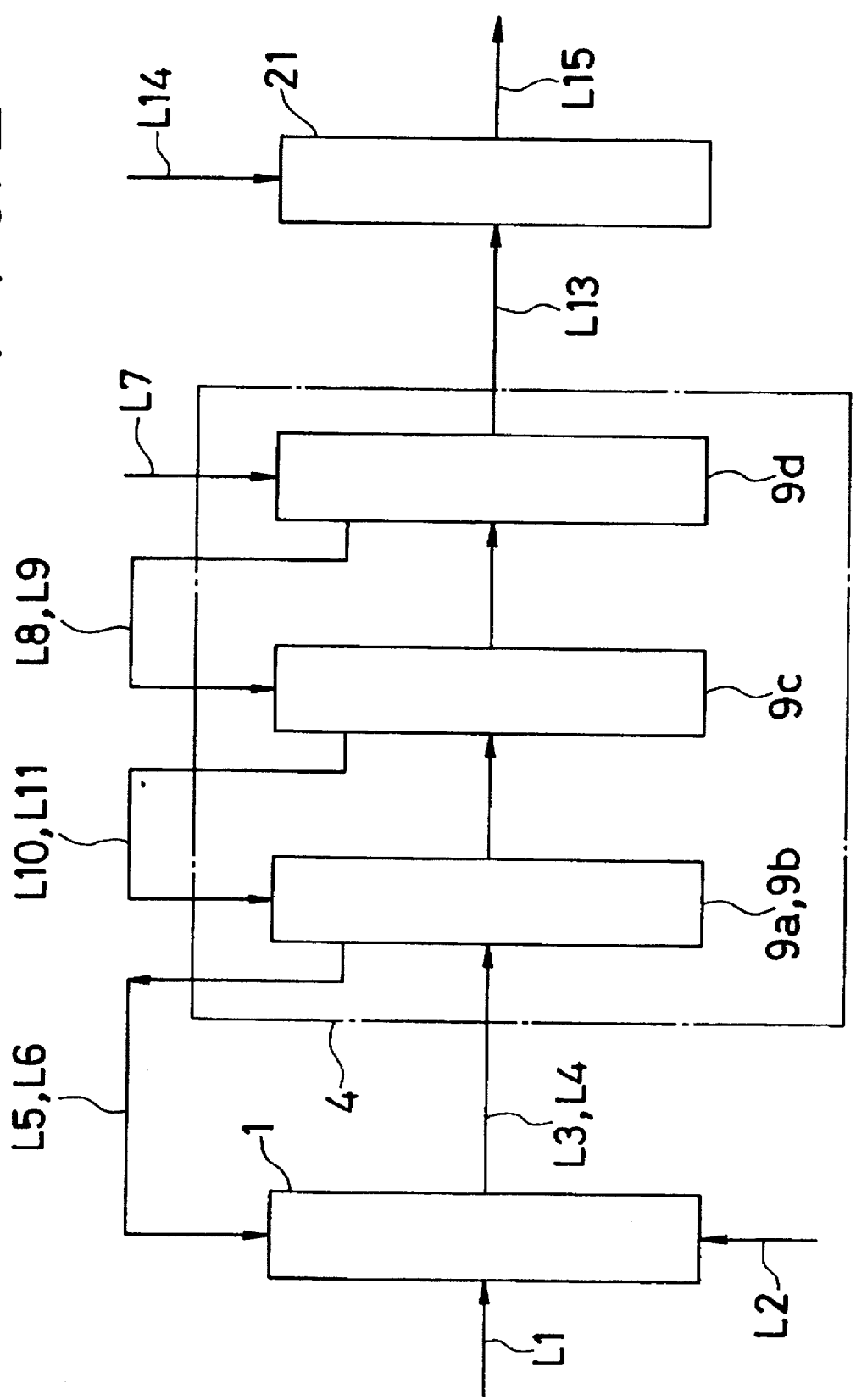
FIG. 2 is a schematic sequence diagram for the method for recovering crystals from a slurry according to the present invention.
Figure 3:
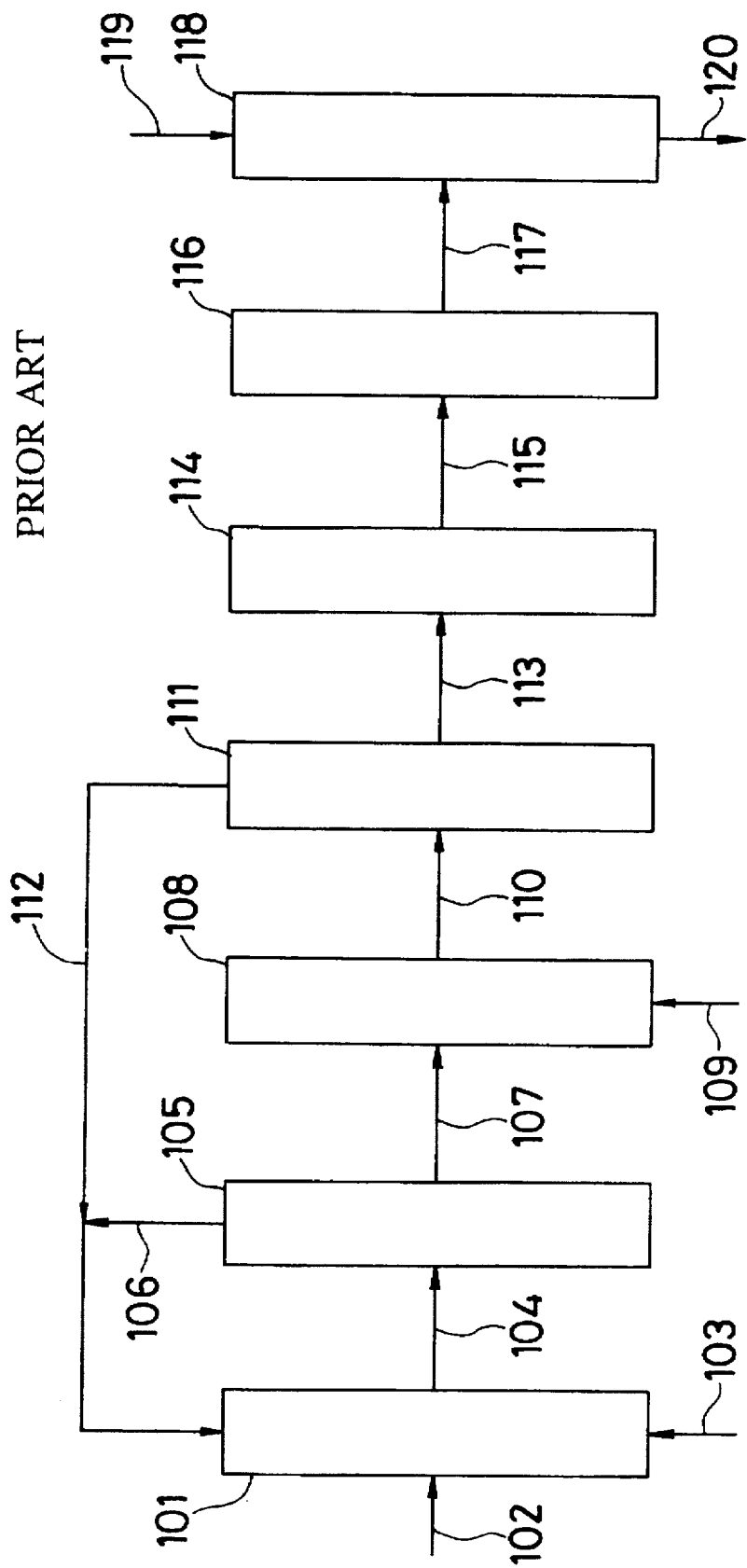
FIG. 3 is a schematic sequence diagram for a typical conventional method for recovering crystals from a slurry.

In FIG. 2, the procedures of the method according to the present invention described above are explained schematically in a flow sequence diagram. As shown, the slurry containing crystals of terephthalic acid formed in the oxidizing reactor 1 is guided to the rotary pressure filter 4 via the line L3,L4. In the rotary pressure filter 4, a plurality of solid/liquid separation steps of filtration and washing purification are performed in the filtering region 9a and the washing regions 9b, 9c and 9d, wherein the washing liquid supplied via the line L7 is used for washing the filter cake in the washing region 9d in the forefront in the rotating direction of the filter medium and the spent washing liquid thereof is used for washing the filter cake in the washing region 9c neighboring the said forefront washing region 9d in the aft side in the rotating direction of the filter medium by supplying it thereto as the washing liquid therefor via the line L8,L9 and, further, the spent washing liquid of this washing region 9c is used for washing the filter cake in the washing region 9b rearmost in the rotating direction of the filter medium by supplying it thereto as the washing liquid therefor via the line L10,L11. The spent washing liquid separated in the washing region 9b rearmost in the rotating direction of the filter medium is returned together with the filtrate from the filtering region 9a to the oxidizing reactor 1 via the line L5,L6. The filter cake of the crystals washed finally by pure water in the washing region 9d in the forefront in the rotating direction is collected and sent to the disperser 21 via the line L13.

As described above, the method according to the present invention can afford to recover crystals from a crystal-containing slurry using a simplified apparatus by a simple operation efficiently with the simultaneous attainment of an effective reclamation of the contaminant components included in between the crystals in the filter cake, such as acetic acid etc., by recovering them at higher concentrations, since the procedures of washing of the filter cake and separation of the spent washing liquid are repeated in a plurality of washing regions settled within the rotary filter by using the spent washing water separated in any one of the washing regions as the washing liquid for the washing region adjacent to the said one washing region on the aft side in the moving direction of the filter medium.

What is claimed is:

1. A method for recovering crystals from a slurry containing the crystals, solvent and a catalyst, using a rotary filter having a rotating cylindrical filter medium, the method comprising the steps of:

pressurizing the outside of the cylindrical filter medium by pressing a gas thereinto, supplying the crystal-containing slurry to the rotary filter from a reactor in which the raw materials are subjected to an oxidation reaction to form the slurry, filtering the supplied slurry in a filtering region of the rotating cylindrical filter medium so as to separate the crystals as a filter cake on the filter medium, washing the filter cake on the rotating cylindrical filter medium in a plurality of washing regions by supplying a washing liquid to, and separating any resulting spent washing liquid from, each of said plurality of washing regions in such a manner that a fresh washing liquid is supplied to a washing region of said plurality that is located at a forefront in the rotating direction of the rotating cylindrical filter medium, while supplying to any one of said plurality of washing regions on an aft side of said forefront, as seen in the rotating direction of the rotating filter medium, with a spent washing liquid separated in a washing region of said plurality that is adjacent to a washing region of said plurality that is on a fore side thereof, as seen in the rotating direction of the filter medium, recycling a spent washing liquid from a washing region of said plurality that is in a rearmost position, as seen in the rotating direction of the rotating cylindrical filter medium, to said reactor together with the filtrate of the filtering region and reusing the solvent and the catalyst contained in the spent washing liquid and in the filtrate, and collecting the washed filter cake from the filter medium.

2. The method as claimed in claim 1, wherein the filtration is carried out in such a manner, that the slurry is supplied to the outside of the cylindrical rotating filter medium while pressurizing a slurry side of the rotary filter.

3. The method as claimed in claim 1, wherein said crystals are crystals of terephthalic acid.

* * * * *